United States Patent [19]
Meyer et al.

[11] 4,092,441
[45] May 30, 1978

[54] ROOFING GRANULE TREATMENT BY COATING WITH A METALLIC ALGICIDE

[75] Inventors: John E. Meyer; David C. Little, both of Hagerstown, Md.

[73] Assignee: GAF Corporation, New York, N.Y.

[21] Appl. No.: 808,100

[22] Filed: Jun. 20, 1977

Related U.S. Application Data

[62] Division of Ser. No. 392,930, Aug. 30, 1973, abandoned.

[51] Int. Cl.$^2$ .......................... B05D 1/00; B05D 1/08
[52] U.S. Cl. ...................................... 427/37; 427/214; 427/217; 428/145; 428/148; 106/15 R; 428/404
[58] Field of Search ............... 428/145, 403, 404, 148; 427/214, 217, 215, 34, 37; 106/15 AF

[56] References Cited

U.S. PATENT DOCUMENTS

| | | | |
|---|---|---|---|
| 3,507,676 | 4/1970 | McMahon | 428/145 |
| 3,528,842 | 9/1970 | Skadulis | 428/145 |

*Primary Examiner*—Ronald H. Smith
*Assistant Examiner*—Sam Silverberg
*Attorney, Agent, or Firm*—Walter C. Kehm; Joshua J. Ward

[57] ABSTRACT

Metal algicides, such as zinc and copper, are sprayed in the form of droplets of molten metal onto the surface of roofing granules or onto the surface of asphalt roofing compositions in which said granules are embedded. The metal algicides solidify and adhere on the surface of said granules or compositions as relatively fine, randomly distributed, irregular shaped metal globules. During periods of rain or dew upon atmospheric exposure of roofing compositions thus flame treated, or incorporating therein roofing granules so treated, the oxidized globules become ionized so that metallic algicidal ions are slowly released therefrom and leached over the roofing surface, thus retarding the biological growth of algae and/or fungi over extended periods of time. The invention permits an effective distribution of algicidal material over the surface treated, requires the use of advantageously low dosage levels of said metals for satisfactory, long-term algicidal action, and provides a high degree of compatibility with the requirements of conventional roofing granule and asphalt roofing composition production.

9 Claims, No Drawings

ROOFING GRANULE TREATMENT BY COATING WITH A METALLIC ALGICIDE

This is a division of application Ser. No. 392,930, filed Aug. 30, 1973 now abandoned.

BACKGROUND OF THE INVENTION

1. Field of the Invention

This invention relates to roofing compositions having algicidal properties. More particularly, it relates to roofing granules and to roofing shingles incorporating said granules and possessing algicidal properties for the effective retardation of the biological growth of algae and/or fungi on roofing surfaces.

2. Description of the Prior Art

Roofing granules, both natural and artificially color-coated granules, are extensively used in roll roofing and asphalt shingle compositions. The roofing granules are generally embedded in the asphalt coating on the surface of an asphalt-impregnated felt base material, the granules thus forming a coating that provides an adherent, weather-resistant exterior roofing surface. As this outer granule coating also provides the esthetic effect observable with respect to the roofing composition, the appearance of the granules is of major marketing interest. For this reason, therefore, a pigmented color coat is ordinarily applied to the base mineral granules to enhance their visual, decorative effect.

As white or light-colored roofs are particularly favored in warmer climates, $TiO_2$ pigment is commonly used in the production of light color-coated roofing granules. In such warmer climates, as in the southern part of the United States, discoloration of asphalt roofing compositions by the growth of algae and/or fungi is of particular concern. Such discoloration, of course, is particularly noticeable on the white or light-colored roofs otherwise so desired and popular in such regions. Upon discoloration, the roof becomes unsightly in appearance and is found to cause a greater heat absorbence as, for example, when a white roof is turned dark brown or black in a period of a few years in use.

Nor is this problem, so widespread in areas such as the southern U.S. particularly the gulf state area, confined necessarily to such regions. Thus, discoloration of roofing surfaces by the growth of algae and/or fungi has also been found in the northern part of U.S., particularly so in areas along rivers and lakes and along the northern coastal regions. While home owners and others have been aware of this discoloration problem for many years, effective, practical solutions thereto have not been forthcoming at a reasonable cost. The problem of roofing granule discoloration, therefore, has remained a major marketing problem for the roofing industry.

For many years, this problem of roofing granule discoloration was believed to be caused only by fungi, as is the case with respect to some outdoor paint surfaces. Many different types of fungi have, in fact, been isolated from discolored roofing surfaces. More recently, however, it has been learned that other organisms contribute principally to this discoloration and have been identified as terrestrial blue-green algae of the Cyanophyta division. Such algae are transferred through the air as spores and/or vegetative matter and deposited on roofing surfaces where they thrive and grow. Natural pigments produced by the algae add to the dark discoloration of the roof, which is generally first noticeable in spots that develop into dark vertical streaks that gradually darken until the entire roof becomes a totally discolored black within five to fifteen years. Predominant algae thus identified from infested roofing shingles include *Gloeocapsa Magma, Tolypothrix Byssoidea, Nostoc sp.* and *Scytonema sp.* In general, metallic algicides that are effective in retarding the biological growth of such algae are likewise effective in similarly retarding the growth of fungi. The incorporation of a metallic algicide in the color coat of roofing granules, therefore, has heretofore been proposed in order to inhibit or prevent the discoloration of roofing surfaces containing such granules as a result of algae and/or fungi growth.

The incorporation of a metallic copper algicide in the color coat of roofing granules was disclosed in the Skadulis patent, U.S. Pat. No. 3,528,842. Skadulis particularly proposes the incorporation of copper algicides that are substantially waterinsoluble but that have limited solubility in acidic solutions, e.g., $Cu_2O$. Similarly, slightly soluble zinc algicides were disclosed for incorporation in the color coat of roofing granules in the McMahon patent, U.S. Pat. No. 3,507,676. As was pointed out in the McMahon patent in Column 2, lines 58–65, such zinc algicides are effective when employed in an amount constituting at least about 1% by weight of the base mineral granules, i.e., about 20 lbs. of the zinc algicide compound or metal per ton of granules. The incorporation of particular copper or zinc algicides in the color coat of roofing granules, in the manner and in the quantities taught by the Skadulis and McMahon patents, imparts a desirable resistance of roofing surfaces containing such granules to discoloration upon exposure to atmospheric weathering. The teachings of these patents, however, have not led to the development, commercial availability and use of algicidal roofing granules providing the desired degree of algae and/or fungi resistance over an extended period of time at economically competitive cost. In part, of course, this unavailability of a totally satisfactory algicidal roofing granule reflects the continual desire in the roofing industry for a more effective algicidal effect from a roofing granule of ever diminishing incremental cost to achieve such an algicidal effect. Any incorporation of metallic algicides in an otherwise conventional roofing granule coating in order to achieve the necessary or desirable algicidal effect necessarily adds an incremental cost to the roofing granule and to the roofing material incorporating such an algicidal granule. While the desired toxic effect is a necessary or highly desirable feature of the algicidal roofing granule, the providing of this property or function is an expense item that, from a marketing viewpoint, must be minimized to the fullest possible extent. The use of minimum quantities of metallic algicides to produce a desired level of effectiveness over an extended period of time is, therefore, highly desirable. While the prior techniques have imparted an algicidal effect to roofing granules, an enhanced effect would provide further assurance of the desired toxic effect, thereby enhancing the quality of such granules. In this regard, it should be noted that the algicidal granules of McMahon require the incorporation of a relatively large amount of zinc for effective algicidal action as noted above. As the amount of metallic algicide required for effective action increases, the cost of the resulting algicidal granule is directly increased thereby. In addition, the use of relatively large amounts of metallic algicides frequently requires the incorporation of pigment in the granule coating in amounts in excess of that otherwise required to achieve a desired roofing granule color. As the amount of $Cu_2O$ employed is increased, for example, the amount of $TiO_2$ pigment that must be employed in the granule coating composition to produce a white roofing granule is also generally increased. Such an additional requirement necessarily adds to the overall cost of the algicidal roofing granule product and of roofing materials made therefrom.

The prior art above is, of course, subject to the practical necessity of producing such algicidal granules as a separate production operation apart from the production of conventional, non-algicidal, color-coated roofing granules because of the variation in the color coating formulation necessarily required to incorporate the algicidal compound into the color coating. The interruption of such conventional roofing granule production and the related scheduling and inventory problems associated therewith tend to create a further economic disadvantage associated with the production and marketing of algicidal roofing granules and roofing compositions incorporating said granules.

In another prior art approach, conventional, non-algicidal granules are employed, and relatively coarse granular zinc or zinc-containing material is blended with said granules prior to the embedding thereof in the asphalt coating of the roofing shingle composition. This approach, disclosed in the Klimboff patent, U.S. Pat. No. 3,598,627, results in the production of an asphalt-impregnated base that contains embedded, on all or a portion of its exterior surface, said granular zinc or a granular zinc-containing material along with the conventional colored granules. The granular zinc is disclosed as having a particle size distribution within the overall range of about $-10+35$ mesh and an effective dosage level of from about 3% to about 10% by weight based on the weight of conventional, colored granules employed. While this approach thus overcomes some of the production, scheduling and inventory problems associated with the incorporation of an algicidal agent in the color coat itself, it will be seen that the relatively high amounts of zinc that must be employed and the nature of the distrubution of the relatively large zinc particles in the asphalt coating along with said conventional granules necessarily produces an incremental cost-algicidal effectiveness relationship not fully satisfying the overall commercial imperatives relating to the marketing of roofing granules and roofing composition, as discussed above. There is a need in the art, therefore, for improved algicidal products and techniques so that effective inhibition or prevention of the discoloration of roofing surfaces due to the growth of algae and/or fungi can be provided in the art with an economically feasible balance between the desired algicidal effectiveness and the incremental cost to achieve such algicidal properties. Such a need must also be satisfied, as indicated above, in a manner permitting optimum flexibility and compatibility with the ordinary requirements of the conventional production of non-algicidal roofing granules and compositions.

It is an object of the present invention, therefore, to provide improved algicidal roofing granules and compositions.

It is another object of the invention to provide an improved process for the production of such algicidal roofing granules and roofing compositions incorporating same.

It is another object of the invention to provide algicidal roofing granules and compositions having effective, long-term algicidal properties at economically desirable, low levels of metallic algicide content.

It is another object of the present invention to provide a process for the production of algicidal roofing granules and roofing compositions incorporating said granules with enhanced operating flexibility and compatibility with the requirements of conventional granule and roofing production operations.

It is a further object of the invention to provide roofing surfaces having an enhanced resistance to discoloration during extended periods of exposure to atmospheric weathering.

With these and other objects in mind, the present invention is hereinafter set forth in detail, the novel features thereof being particularly pointed out in the appended claims.

SUMMARY OF THE INVENTION

Effective algicidal properties are imparted to roofing granules at low dosage levels and with optimum processing flexibility and compatibility with conventional roofing operations by spraying fine droplets of molten algicides onto the surfaces of such granules. The metal algicides are sprayed onto roofing granules prior to their incorporation in asphalt roofing surfaces, with the molten metal droplets solidifying on the granules as randomly distributed, relatively fine, irregularly shaped globules. The metal algicide is thereby effectively distributed for highly desirable algicidal effect in retarding unsightly discoloration of the roofing surface due to algae and/or fungi growth during prolonged atmospheric exposure of said roofing surface during service, especially in warm, humid environments conducive to the growth of such algae and/or fungi. The metal algicide can be readily applied to the roofing granules without appreciable disruption of conventional operations, thus minimizing production, scheduling and inventory problems that may be associated with the accommodation of conventional granule production operations to the production of algicidal granules. As the spraying of algicide in accordance with the invention permits advantageously low dosage levels of the algicide to be employed, the incremental cost of imparting algicidal properties to the granules is also minimized.

DETAILED DESCRIPTION OF THE INVENTION

In the practice of the present invention, highly desirable algicidal properties are imparted to roofing granules in a manner providing enhanced effectiveness, economy and compatibility with commercial roofing granule operations. Roofing surfaces containing granules so treated, release algicidal ions slowly over an extended period of time during periods of rain or dew upon exposure to atmospheric weathering. The roofing surface is thus rendered resistant to unsightly discoloration due to infestation and growth of algae and/or fungi, said treated surfaces being of particular interest in humid environments normally conducive to the growth of algae and/or fungi.

Any suitable base raw mineral granules commonly employed, such as greenstone or netheline syenite, can be used in the practice of the present invention. While uncolored granules can be used, artificially colored granules are commonly employed in commercial roofing applications. For this purpose, an alkali metal silicate-clay coating is applied to the base mineral granules and fired to produce a moisture permeable, substantially water insoluble, durable, pigmented coating on the base mineral granules. As the techniques for the application of a color coating to the raw granules are well known in the art and form no part of the present invention, no detailed disclosure relating thereto is included herein. In ordinary commercial operations, the color coated granules are generally post treated with a processing oil and/or a coating composition as is known in the art and permissible in the practice of the present invention.

As applied to roofing surfaces containing such mineral granules, the present invention contemplates the imparting of algicidal properties to the granules prior to their incorporation in the roofing surface. The flexibility inherent in the process of the present invention represents an important feature providing a high degree of compatibility with the requirements of conventional roofing granule production, as where the scheduling of the production of conventional granules and of algicidal granules, the availability of production lines, and the requirements and restrictions of inventory and sales may be important factors in practical, commercial roofing applications.

Roofing granules are commonly employed by incorporation in conventional asphaltic roofing compositions, such as roofing shingles, rolled roofing, and the like. Such compositions typically have an organic asphalt-saturated felt base that is coated with an asphalt of a higher softening point and surfaced with color coated or other roofing granules, such as conventional non-algicidal roofing granules or algicidal roofing granules, such as the novel algicidal granules employed in particular embodiments of the invention. As the compositions of the felt layer, the saturants employed therewith and the asphalt coatings for the saturated felt are all very well known and established in the art and form no essential part of the novel aspects of the invention, a detailed disclosure with respect thereto is not included herein. Upon application of the asphalt coating to the saturated felt layer and the application of the roofing granules thereto, the resulting roofing surface is then passed through suitable rollers and presses, quenched and otherwise treated and handled in accordance with conventional practices in the roofing industry. It will be appreciated that numerous variations in the production of the desired roofing composition and in the additive materials employed therein are well known in the art and can be employed within the scope of the present invention.

Algicidal properties are imparted to the roofing granules in accordance with the present invention by spraying zinc, copper and/or other metal algicides onto the surfaces being treated in the form of droplets of molten metal. The molten metal algicides solidify and adhere to the surface of the granules as relatively fine, randomly distributed, irregular shaped metal globules. Upon exposure of roofing compositions containing granules so treated to atmospheric weathering, the fine metal algicide globules are oxidized but are not dislodged or washed off to any appreciable extent in ordinary use or during periods of heavy rain. Upon exposure to moisture during periods of rain and dew, however, the oxidized metallic algicides become ionized and slowly release metallic algicidal ions having a toxic effect on the biological growth of algae and/or fungi. Because of the slow rate at which metallic algicidal ions are released from the fine globules of oxidized metal adhering to the roofing granules, such fine algicidal globules are effective over very extended periods of time in actual use in roofing applications. The release of such algicidal ions and the leaching thereof over the roofing surface produces the desired effect of prohibiting or effectively retarding the biological growth of algae and/or fungi on the roofing surface. It will be appreciated that metal algicides having varying rates of leachability can be employed in the practice of the invention, alone or in combination, to achieve the desired effect in prohibiting and retarding the biological growth of algae and/or fungi. In addition, the irregular shape of the solidified metal globules contributes to a desirable variation in ion leach rate, thus enhancing the advantageous long term algicidal-inhibiting effect of the algicides. It will be appreciated, in this regard, that some of the globules will be very fine, while others will be significantly larger, generally within the particle size range hereinafter indicated. As the relatively smaller globules will have a greater surface area than the larger globules, algicidal ions will tend to be released initially more readily from said finer globules than from the relatively larger globules dispersed therewith over the roofing surface.

The algicides solidified on the treated surfaces as randomly distributed, relatively fine, irregular shaped globules are found, because of these characteristics, to achieve superior distribution over the treated surfaces together with enhanced leachability. As a result of such effective utilization of the algicides, in accordance with the present invention, the amount of algicide material employed can also be minimized. An overall combination of enhanced properties and operating effects is thus achieved. The invention thereby represents a significant advance in the industry effort to enhance the effective algicidal properties of roofing granules, while minimizing the incremental cost of achieving such properties. As disclosed herein, the present invention permits this advantageous combination of desirable features to be readily obtained with the additional advantage of enhanced operating flexibility and compatibility with the requirements of conventional roofing operations and the anticipated needs of roofing compositions in any given application for desirable protection against the unsightly discoloration resulting from the biological growth of algae and/or fungi.

It is within the scope of the invention to spray droplets of any metallic algicidal material that can readily be sprayed in molten form and that will solidify on the treated granules as globules that will oxidize and release algicidal ions upon exposure to rain and dew upon atmospheric exposure and use in roofing compositions. While cadmium, silver and other such materials can be employed in the practice of the invention, however, it is generally preferred to employ zinc, copper and nickel as the metal algicides to achieve an advantageous combination of highly effective algicidal action and relatively low incremental cost. It will also be appreciated that a combination of metal algicides can be employed in a given application. In spraying such metal algicide(s) onto the surface of the granules, any suitable, commercially available apparatus may be employed, the mechanical features of the apparatus for spraying molten metal droplets of algicidal material onto the granules not being critical to the novel features of the invention. One suitable technique for spraying the molten metal droplets onto the roofing granules, as herein contemplated, is by the use of a flame spray gun, such as the Metco Type 7E flame spray gun marketed by Metco, Inc. Such a spray gun can be adjusted so that the feed rate of metal wire, the balance of fuel and oxygen, the nozzle openings, and the distance between the gun and the granules being treated are such as to apply the metal algicide material to the granules at the desired dosage level and with the desired size for the purposes of the present invention. It will be appreciated, for example, that if the distance between the flame spray gun and the granules being treated, under given flame spray temperature and velocity conditions, is too far apart, the metal droplets may tend to cool and solidify sufficiently to interfere with their adherence to the granules, while, at too close a separation of flame gun and granules, the droplets may tend to splash off the granules upon impact. While those skilled in the art will appreciate that the flame spray gun placement will depend upon a number of factors related to any given application, it has generally been found generally desirable to position the flame gun from about 4 inches to about 10 inches, conveniently about 6 inches, from the granules being treated for convenient application of the metal algicides to the granule surfaces.

Another feasible technique for spraying molten metal algicides onto the roofing granules being treated involves the use of commercially available electric arc guns in which, for example, two zinc wires can be shorted and a jet of air employed to spray the molten metal in droplet form onto the granules. The arc gun, which can be operated similarly under desired conditions and at a desired distance to enhance the adherence of the molten particles on the granule surfaces, appears to result in the formation of slightly coarser globules and to offer other possible operating advantages.

Regardless of the particular apparatus employed to spray the molten metal onto the granules, it is important that the granules be in dry form to facilitate the adherence of the metal droplets to the granule surfaces. In this regard, it should be noted that the metal algicide can be sprayed onto the granules either before or after the conventional posttreatment operation in which a processing oil or a coating composition is applied to the granules to enhance their storage, flow and handling properties and their subsequent, effectiveness in asphaltic roofing compositions. In either event, the granules should be dry at the time of algicidal spray treatment and can conveniently be at an elevated temperature, e.g., about 150° F, at the time of the spraying of the metal algicide thereon to assure the desired dryness. While the granules can thus be sprayed while in a warm, dry condition following the firing of the color coating, it is generally preferred to spray the granules with the molten algicide following the conventional post treatment operation and the requisite drying of the thus post-treated granules. The granules, at the time of algicidal treatment, can be in any convenient position to facilitate the desired spraying thereof with molten algicidal metal in droplet form. While the granules can thus be in a rotary batch mixer at the time of spraying with algicide, this arrangement does not lend itself particularly to practical operations on a continuous production basis, and the spraying of the algicide droplets onto the granules passing along a vibrating conveyor belt or like conveyance is generally preferred from a practical operating viewpoint.

Attention is drawn to the fact that the present invention can be practiced to produce algicidal roofing granules suitable for incorporating in various embodiments of asphaltic roofing compositions having desirable long-term resistance to discoloration due to the biological growth of algae and/or fungi. In one embodiment, all of the roofing granules to be incorporated in the roofing composition can be sprayed with fine droplets of molten metal at the advantageously low dosage levels permissible in the practice of the invention. In another embodiment, masterbatch granules can be sprayed with a heavier dosage of algicidal metal, said masterbatch granules thereafter being blended with untreated granules to achieve the desired random distribution and dosage level over the surface of the asphaltic roofing incorporating therein the blend of masterbatch treated granules and untreated granules. In another embodiment, the masterbatch granules can be employed in a concentrated area of the roofing composition, as for example in a shadow line effect by placement along the transition between the butt and head portions of roofing shingles. For all such embodiments, the application to the granules of the metal algicides in the form of droplets of molten metal, as herein provided, provides for an effective distribution of algicides in the form of relatively fine, randomly distributed, irregular shaped metal globules. Because of the advantageous algicidal action resulting from the slow releasing of algicidal ions from said globules and their leaching over the surface of the roofing composition, the present invention provides a highly desirable advance in the art, with the desired algicidal action being accomplished at very low dosage levels of required algicidal material, thus minimizing the incremental cost of providing protection against undesired discoloration resulting from the biological growth of algae and/or fungi.

In asphaltic roofing compositions, mineral granules, typically color coated granules, are employed in commercially established quantities, e.g., generally on the order of about 35 pounds of granules per square or 100 $ft^2$ of shingle butt portion. It will be appreciated that the exact amount of granules employed may vary depending on the particular operations of a given roofing manufacturer, the particular shingle or other roofing product involved and other pertinent factors relating to any specific roofing operation. With respect to the treatment of the roofing granules to impart algae resistance thereto prior to the incorporation thereof in asphaltic roofing compositions, the present invention permits advantageously low levels of metal algicides to be sprayed onto the granules although, of course, greater algicide dosage levels can be employed without departing from the scope of the invention herein disclosed and claimed. Similarly, very low algicide dosage levels can be employed although it will be appreciated that such low levels can be reached as to preclude, in practical operating terms, the effective, long term algicidal action desired over the surface of the asphaltic roofing composition incorporating the treated algicidal granules. For algicidal granules to be distributed across the entire butt portion of the roofing shingle or other exposed asphaltic roofing surface, the metal algicide dosage level will generally range from about 0.5 to about 12 pounds per ton of granules, i.e., 57 squares of shingle. Preferably, the algicide dosage level will range from about 1 to about 8 pounds per ton of granules, with a dosage level of from about 2 to about 6 pounds of algicide per ton of granules being generally preferred for many practical commercial roofing applications. As indicated above, however, it is within the scope of the invention to prepare masterbatch quantities of treated granules for subsequent blending with untreated granules, use for shadow line effect, or the like. For such purposes, of course, the dosage level of molten metal algicide sprayed onto the granules will be greater than the ranges indicated above, although the amount of such masterbatch treated granules employed in the overall asphaltic roofing composition will generally be such that the total amount of algicide present on the overall roofing composition will be on the same order of magnitude as that present in roofing compositions having granules at the aboveindicated lower, non-masterbatch dosage levels incorporated across the surface of the asphaltic roofing composition. For masterbatch granule purposes, the metal algicide dosage level will range from about 12 to about 50 pounds per ton of granules or more, with amounts of from about 20 to about 30, typically on the order of about 25 pounds per ton of granules being generally satisfactory for many algicidal roofing applications.

It should be noted that the spray of molten metal algicides will include a random particle size ranging from a very fine mist up to rather large droplets. Due to such variation and to the random manner in which the molten algicides contact, solidify and adhere to the granule surfaces, the solidified globules will be very irregularly shaped and of a random size distribution. While some of the metal droplets may solidify in spherical form, others may solidify in irregular shape due to distortions upon impact with the granule surface, the blending of individual droplets and the like. It is such irregularity of metal globule size and shape that contributes to the desirable variation in the rate of ion release and leaching referred to above with respect to the ability of the algicidal granules to inhibit the biological growth of algae and/or fungi over an extended period of time upon exposure to atmospheric weathering in asphaltic roofing compositions. In this regard, it should be noted that the coverage of the algicidal globules on individual roofing granule surfaces will vary considerably with non-masterbatch granules having coverage typically of from about 1% of the exposed surface area for very large granules up to about 50% on small granules, while the more heavily treated masterbatch granules having surface area coverage perhaps ranging from about 25% to about 100% on individual granules. It will be appreciated, however, that such coverage will vary widely due to the random nature of the algicidal spray inherent in the practice of the invention.

The conventional roofing granules employed in the roofing industry have an overall particle size distribution typically of on the order of −8 to +40 mesh, U.S. Sieve Series, although it will be appreciated that the overall distribution range and the particular particle size distribution with such overall range will vary depending upon the circumstances of any given mineral granule operation and application. The globules of solidified algicidal metal applied to the granule surfaces as provided in the practice of the invention will be of very much smaller size compared with the size of the granules themselves. Thus, the metal algicide will range from very minute globules up to relatively large, irregularly shaped globules that are nevertheless generally very much smaller than the granules, although it will be understood that, particularly in the masterbatch granules, individual droplets may tend to blend together and solidify in relatively large, irregular shaped globules. While subject to considerable variation due to the inherently random nature of the spraying of molten droplets herein provided, the solidified globules will tend to range in size from on the order of about 14 microns, i.e., about 100 mesh, to very fine, submicron size globules. Despite the inherent variations in size and shape, therefore, it will be understood by those skilled in the art that the solidified globules of metal algicides will be of generally minute size as compared to the conventional roofing granules upon which they adhere.

The highly advantageous benefits achieved in the practice of the invention are illustrated in laboratory experiments and field evaluations of asphaltic roofing shingles containing algicidal roofing granules prepared as herein provided by the flame spraying and the electric arc spraying of zinc and copper metal droplets onto conventional color coated roofing granules following the customary post treatment and drying thereof. As is well known in the art, such conventional granules comprise base mineral granules having a moisture permeable, durable, water insolubilized, pigmented, fired inorganic alkali metal silicate-clay coating thereon. By spraying such droplets as a fine spray from a distance of for example about 6 inches, a representative algicidal content of about 6 pounds per ton of granules was imparted to the treated granules in the form of very fine, randomly distributed, irregularly shaped globules of generally minute size ranging from about 14 microns to submicron size adhering to the surfaces of granules on the order of −8 to +40, i.e., 420 microns, in size. Field evaluations are carried out in the United States and elsewhere under conditions highly conducive to rapid algae development. Periodic evaluations of such sample shingles, or test panels, is made to observe comparative effects that can be reasonably related to the known performance of conventional roofing granules in ordinary roofing usage under generally applicable weathering conditions. For comparative purposes, the algicidal roofing granules of the invention are compared with one another at varying metallic algicidal contents and with control granules exposed for the same period of time under the same set of atmospheric conditions. Such evaluations serve to establish the algicidal effectiveness of the granules of the invention. The adherence of the metal globules is not adversely affected by the oxidation of said globules or by the weathering away of the post-treatment processing oil. Over extended periods of exposure to atmospheric weathering, the algicidal roofing granules of the invention are found particularly effective in inhibiting or preventing the growth of algae and/or fungi. During periods of rain or dew, the oxidized metallic globules become ionized upon exposure to atmospheric moisture, thus slowly releasing metallic algicidal ions that are leached over the surface of the sample roofing shingles or panels. Such ionization and release of algicidal ions do not occur at such a rapid rate, however, as to deplete the available supply of algicidal ions for effective algicidal control over the reasonable life of a roofing composition. In other illustrative examples of the invention, masterbatch granules are prepared with, for example, a dosage level of zinc globules of about 25 pounds of zinc per ton of dry color coated granules. Such masterbatch granules are thereafter blended with untreated granules prior to incorporation in an asphaltic roofing shingle composition, with the masterbatch and untreated granules being blended in such proportions as to provide the same overall zinc content over the overall test shingle or panel as in the previous example. The masterbatch algicidal roofing granules are found to enhance the resistance of the test panel to algae and/or fungi discoloration to a commercially satisfactory extent over an extended period of exposure corresponding to the reasonable life of asphaltic roofing compositions.

It will be understood that various changes and modifications can be made within the scope of the invention herein disclosed and claimed. For example, a combination of algicidal metals, e.g., copper and zinc or zinc and nickel, can be sprayed onto the surfaces of the granules being treated as by the use of two or more spray guns suitably positioned along a vibrating conveyor belt or otherwise so as to apply the desired overall dosage of metallic algicides to the granules. The slow release of a combination of ions produces a bimetallic toxic effect that is particularly effective in retarding the biological growth of algae and/or fungi. It will also be understood that molten metal algicides can also be sprayed in droplet form onto the surface of asphaltic roofing compositions or the butt portion thereof following the incorporation of mineral granules therein. In this instance, the solidified, irregularly shaped globules will be randomly distributed in very fine form over the entire roofing surface, including both the granules incorporated therein and the asphaltic coating in which said granules are embedded. As this approach serves to spray only the exposed portions of the roofing granules rather than the overall granule as in the embodiments discussed above, it may be possible to reduce the necessary algicide dosage level for any desired degree of protection against algae and/or fungi discoloration, even to the point of employing on the order of about half of the algicidal material indicated above. It should also be noted that metallic algicides can similarly be sprayed on other types of roofing or siding materials, such as on terra-cotta roofing, asbestos cement-type roofing or siding materials, vinyl sidings and the like, to provide effective algicidal action upon atmospheric exposure over extended periods of time.

Those skilled in the art will appreciate that a balance must necessarily be drawn between a desired level of algicidal control or protection and the incremental cost of employing algicidal granules in light of pertinent overall marketing considerations. Thus, the degree of algae control achieved, the significance of such control in terms of the ordinary life of the roofing surface, the esthetic effect of even moderate algae growth, particularly on white or light colored roofs, including the objective marketing effect of any unsightly algae and/or fungi discoloration, all in light of the necessary incremental increase in the cost of roofing compositions to achieve whatever degree of algae control is obtained, are all pertinent factors in determining the commercial significance of a novel algicidal roofing granule. The present invention is found to achieve a highly advantageous balance of such pertinent factors, providing a highly effective algae and/or fungi inhibiting effect at minimal incremental cost, together with enhanced flexibility and compatibility with conventional granule production operations. In this latter regard, it will be seen that the process of the present invention can be carried out at the later stage of conventional granule production operations with minimum description of such operations. Algicidal roofing granules can thus be readily prepared as desired in the course of conventional granule production operations, with the scheduling, handling and storage of algicidal roofing granules being readily accomplished in a manner further minimizing the associated incremental expense in providing a premium algicidal granule for effective resistance to unsightly discoloration during extended exposure to atmospheric weathering over the effective life of the asphaltic roofing composition even in humid environments conducive to the growth of algae and/or fungi. The present invention in all of its aspects is, therefore, of major significance to the roofing industry.

Therefore, we claim:

1. A process for the production of algicidal roofing granules having an enhanced ability, over an extended period of time, to leach algicidal ions to inhibit or prevent the growth of discoloring algae and fungi organisms upon atmospheric exposure of roofing surfaces containing such granules, comprising spraying metal algicides in the form of droplets of molten metal onto essentially dry roofing granules, said granules comprising base mineral granules having a size range between about 40 and about 8 mesh coated with a moisture permeable, water insolubilized, pigmented, fired inorganic alkali metal silicateclay coating, said metal algicides adhering to the surface of said granules in the form of very fine, irregularly shaped, randomly distributed solidified globules having a random size range from submicron to about 100 mesh, whereby said globules become oxidized and are capable of slowly releasing metallic algicidal ions upon exposure to moisture during atmospheric weathering, said ions thus being leached over the roofing surfaces in which said granules are employed to retard or prevent the growth of algae and fungi.

2. The process of claim 1 in which said droplets of molten metal are flame sprayed onto the granules being treated.

3. The process of claim 1 in which said algicidal metal is formed into molten droplets by means of an electric arc.

4. The process of claim 1 in which said metal is sprayed onto the granules in an amount within the range of from about 0.5 to about 50 pounds of algicidal metal per ton of base mineral granules.

5. The process of claim 4 in which said metal sprayed is from about 1 to about 8 pounds of algicidal metal per ton of said granules.

6. The process of claim 4 in which said algicidal metal is taken from the group consisting of zinc, copper, nickel and mixtures thereof.

7. The process of claim 6 in which said metal comprises zinc.

8. The process of claim 6 in which said metal comprises copper.

9. The process of claim 6 in which said algicidal metal is sprayed onto said essentially dry granules subsequent to the post treatment of the coated granules with a processing liquid forming a thin film on the surface thereof to enhance the flow and handling properties of said granules.

* * * * *